United States Patent [19]

Brüsewitz et al.

[11] Patent Number: 4,690,896

[45] Date of Patent: Sep. 1, 1987

[54] DEVICE FOR THE DETERMINATION OF MICRO-ORGANISMS

[75] Inventors: Gerhard Brüsewitz, Bergisch-Gladbach; Reinhard Sieck, Cologne, both of Fed. Rep. of Germany

[73] Assignee: Madaus & Co., Cologne, Fed. Rep. of Germany

[21] Appl. No.: 696,533

[22] Filed: Jan. 30, 1985

[30] Foreign Application Priority Data

Mar. 26, 1984 [DE] Fed. Rep. of Germany ....... 3411072
Sep. 22, 1984 [DE] Fed. Rep. of Germany ....... 3434851

[51] Int. Cl.[4] .............................................. C12M 1/30
[52] U.S. Cl. .................................... 435/296; 435/299; 435/300
[58] Field of Search ............... 435/296, 299, 292, 293, 435/298, 300, 301, 800, 803

[56] References Cited

U.S. PATENT DOCUMENTS

| 3,589,983 | 6/1971 | Holderith et al. | 435/296 |
| 3,651,926 | 3/1972 | Elfast, Jr. | 435/296 |
| 3,701,717 | 10/1972 | Ingvorsen | 435/296 |
| 4,218,534 | 8/1980 | La Belle et al. | 435/299 |
| 4,271,270 | 6/1981 | Lukacsek | 435/299 |

FOREIGN PATENT DOCUMENTS 2098626 11/1982 United Kingdom ............... 435/296

*Primary Examiner*—James C. Yeung
*Attorney, Agent, or Firm*—Felfe & Lynch

[57] ABSTRACT

The present invention provides a device for the determination of micro-organisms, comprising a vessel (1) closable with a cover (3) in which vessel is housed a nutrient medium carrier in the form of a longitudinal carrier body (2, 40) which has a plurality of troughs (10, 11, 12, 13, 41, 42, 45, 46) for the reception of nutrient substrate substances, the upper surfaces of which are provided with a removable cover, wherein at least one closable filler connection (19, 20, 43, 44), formed on the carrier body (2, 40) opens into each trough (10, 11, 12, 13, 41, 42, 45, 46).

2 Claims, 16 Drawing Figures

FIG. 1
FIG. 2
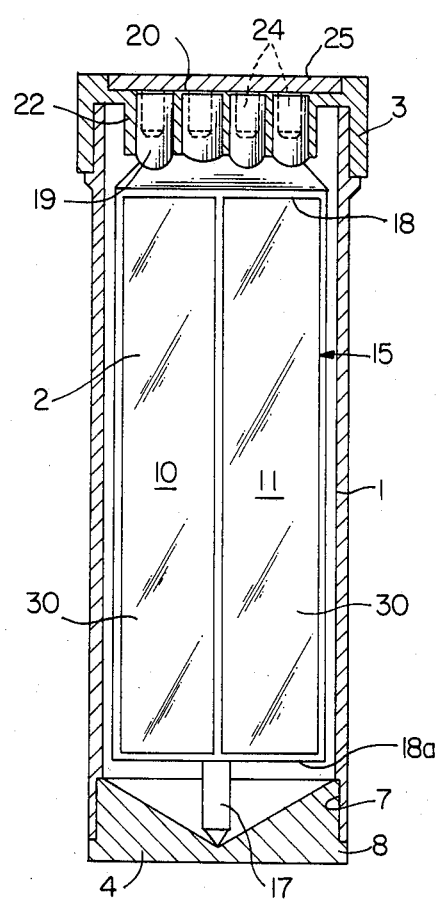
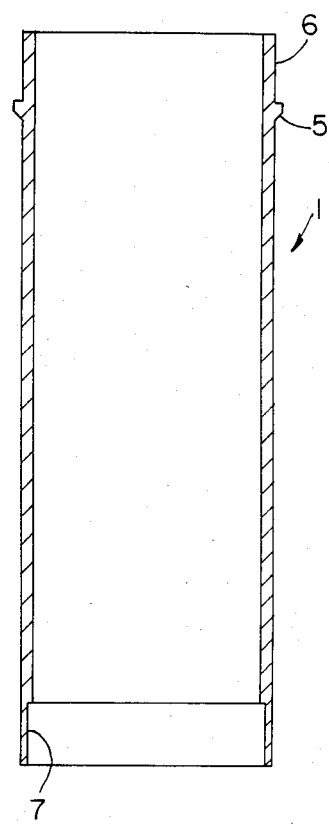
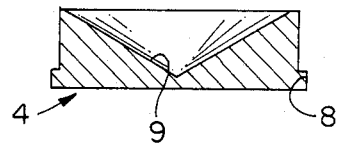
FIG. 11

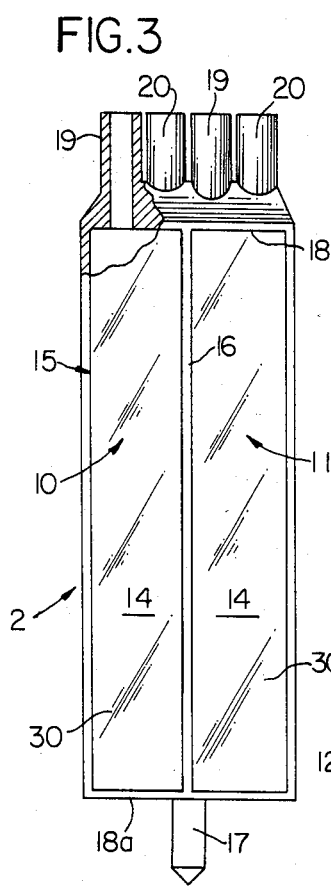
FIG.3
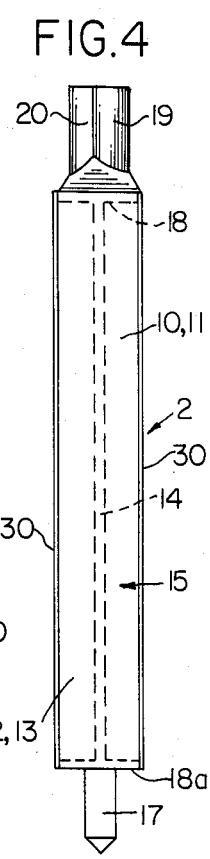
FIG.4
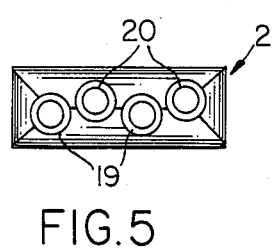
FIG.5
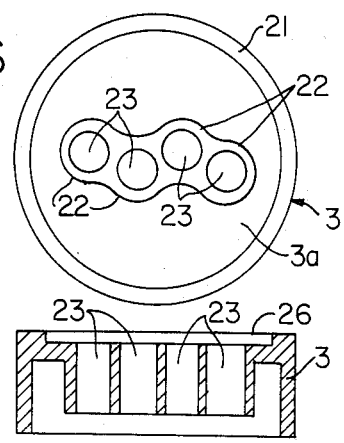
FIG.6
FIG.7
FIG.10
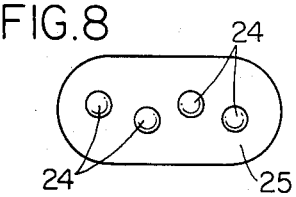
FIG.8
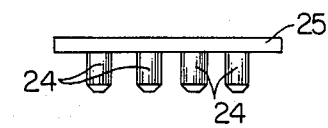
FIG.9

DEVICE FOR THE DETERMINATION OF MICRO-ORGANISMS

The present invention relates to a device for the determination of micro-organisms, preferably comprising a vessel closable by a lid, in which vessel is placed a nutrient medium carrier in the form of an elongated or longitudinal carrier body which has a plurality of troughs for the reception of nutrient medium substances, the upper side of the troughs being provided with a removable cover.

Such devices are supplied to the users, for example physicians, with the same or different nutrient medium substances placed in the troughs, the carrier body being present in the closed, case-like vessel. They are used for diagnostic purposes and for testing for the content of micro-organisms in industrial processes, as well as for hygiene control, as immersion or dabbed-on nutrient substrates, agar-agar being a typical nutrient substrate substance.

A certain difficulty in the production of such devices consists in the critical behavior of the nutrient substrate substances which, for the achievement of their full effectiveness, should, when used, not be dried out and must have the original homogeneity of their surface. In order to prevent an evaporation of water from the nutrient substrate and to avoid collected condensed water from reaching the surface of the nutrient substrate and impairing its homogeneity, the carrier body coated with nutrient substrate is enveloped by a covering which can easily be removed prior to inoculation (see Federal Republic of Germany Patent Specification No. 31 19 541). The covering thereby consists of a water-impermeable plastics film in the form of a rigid, completely closed collar which leaves free no space or, in comparison with the total volume of the vessel, only a small space between itself and the coated carrier body so that no volume or only a relatively small volume, referred to the total volume of the vessel, is available to take up water vapor from the nutrient substrate. In this way, a premature spoiling of the nutrient substrate substances by drying out or by running or splashing condensed water can admittedly be substantially prevented but it is, nevertheless, difficult to carry out the filling of the troughs with possibly different nutrient substrate substances, the cooling thereof and the application of the covering, as well as the placing of the finally prepared carrier body into the vessel under absolutely micro-organism-free conditions. This difficulty arises essentially due to the laborious nature of the filling of the troughs and the confectioning of the device, caused by the construction thereof. In the case of the known device, this takes place by coating the carrier body with nutrient substrate substance either before or after putting on the rigid covering over the carrier body, connecting the vessel lid with the carrier body, placing the carrier body into the vessel and closing the vessel with the vessel lid.

In the case of commercially available devices, coverings are absent and the nutrient substrate substance is arranged, with free, uncovered surface, in the troughs of the carrier body which, for its part, is placed in a container closed with a screwed-on lid. Especially in cases of comparatively long storage, sterility losses hereby occur, which falsify the result of medical micro-organism count determinations.

It is an object of the present invention so to construct a device of the initially-mentioned type that all steps in the production thereof can be carried out mechanically under micro-organism-free conditions, which device can be stored for a long time without impairment of sterility.

Thus, according to the present invention, there is provided a device for the determination of micro-organisms, comprising a vessel closable with a cover in which vessel is housed a nutrient medium carrier in the form of a longitudinal carrier body which has a plurality of troughs for the reception of nutrient substrate substances, the upper surfaces of which are provided with a removable covering, wherein at least one closable filler connection, formed on the carrier body, opens into each trough.

In this way, it is possible mechanically to fill, under sterile conditions, the troughs, provided with the covering and thus closed on all sides and closed off against each other, with nutrient substrate substances by means of hollow needles inserted into the filler connections. Through the individual filler connections opening into the troughs and independent of one another, there are introduced various nutrient substrate substances into the troughs, strictly separated from one another, so that each nutrient substrate retains its specific properties and undesired depositions of nutrient substrate components do not arise. The troughs of the carrier body are preferably filled with the troughs placed in the vessel so that, after completion of the filling procedure, only the filler connections and the vessel have to be closed. Since this can also be carried out mechanically under sterile conditions, after removal of the cover, the user of the device has available an absolutely micro-organism-free grouping of nutrient substrates, the nutrient substrate substances of which are fully effective for the qualitative and quantitative determination of micro-organisms, preferably of pathogens, which, after incubation, can be evaluated in the usual manner. Because of its micro-organism-free preparation, the storage stability of the device is considerably improved.

Advantageously, the carrier body has several longitudinally-running troughs on its periphery and all the filler connections are arranged on an end face of the carrier body.

In the case of one embodiment of the present invention, each filler connection is formed as a tubelet, the closure means therefor being on the cover. The carrier body can be plate-shaped with troughs arranged on both wide sides, the tubelet-shaped filler connections thereby being advantageously arranged on the end face of the carrier body in staggered relationship to one another. Therefore, in the case of at least two troughs on each surface of the carrier body, a line running through the middle points of the filler connections has a wavy form. Due to the staggered arrangement of the filler connections, space is gained and the diameter of the identical filler connections can be sufficiently large in order to make possible a rapid filling of the troughs with the help of hollow needles.

From the inner surface of the closed base of the cap-shaped cover, there project collars or plugs which fittingly engage with the tubelet-shaped filler connections. These collars or plugs can serve as closure means for the tubelet-shaped filler connections. Furthermore, they firmly hold the carrier body standing in the vessel and prevent disadvantageous shaking movements for the nutrient substrate substances during transport or the like.

In a further advantageous embodiment of the present invention, it is provided that, from the inner surface of the base of the cap-shaped cover, there project collars which fit over the tubelet-shaped filler connections and that, in the base of the cover, there are formed passages which align with the collars and in which are arranged plugs penetrating into the filler connections, these plugs being formed on a plate fittingly let into the outer surface of the base of the cover. In this case, the closure parts for the filler connections provided on the cover are formed as plugs which, independently of the cover closing the vessel, can be introduced into the openings of the filler connections for the closure thereof. Because of this construction, it is possible to close the vessel containing the carrier body with covered troughs with the cover and to fill the troughs through the passages in the bottom of the cover. Since the collars pass over the filler connections, the carrier body is stable and the canal leading into the troughs is sealed off from the inner chamber of the vessel so that the nutrient substrate substance exclusively gets into the trough in question. As soon as the troughs are filled, the plate with the plugs is introduced into a depression in the outer surface of the bottom of the cover and the plugs penetrate as closure stoppers into the filler connections.

After production has taken place, there can be carried out an additional closure of the device by welding, be it by hot welding or utltra-sonic welding, with a synthetic resin cover or with a film. This working step is to follow directly the filling of the troughs and can be integrated in a filling machine.

In the case of a further embodiment of the present invention, it is provided that all troughs continue up to the filling end of the carrier body and, for the formation of the filler connections, are enclosed by a common surrounding wall for a short part of their length, which wall follows the cross-sectional shape of the carrier body. On the intersection of all troughs there is formed, in the region of the filler connections, an axial blind hole in which engages an axial pin which projects from the screwable cover of the vessel. This device is simple to produce and can also be filled and closed under completely sterile conditions.

On the end of the carrier body remote from the filler connections, there is provided a centering mandrel which engages in a central bottom trough of the vessel. This centering means stabilizes the carrier body in the vessel and prevents tilting during the filling of the carrier body standing in the vessel according to the first embodiment.

According to the present invention, a further very substantial improvement of the device consists in that the removable covering consists of a thin, flexible film which is sealingly connected with the carrier body, this flexible film being made, for example, of a synthetic resin or of a metal, such as aluminum. It can thereby be a leaf-like flexible film and a separate, individually removable film leaf can be provided for each trough. For the sealing connection of the film leaf with the carrier body, its circumferential edge is firmly welded or stuck all round to the edge of each trough. In the case of this manner of covering, each trough is individually accessible and the contents of the other troughs remain sterile until needed. The leaf-like flexible film can also cover several troughs and the filling-side openings of the filler connections can also be tightly closed by a film leaf.

Alternatively, the flexible film can be formed as a tube which tightly envelops the carrier body. This mode of covering simplifies the production of the device.

Furthermore, the construction of the device according to the present invention makes possible the filling of nutrient broth with the help of a computer-controlled filling plant. In this case, after the bacteriological screening, colonies can be inoculated and subjected to a dilution spreading out in order that individual colonies are thereby available. These individual colonies are now inoculated from a plate and introduced into a Mueller-Hinton broth where the micro-organism suspension must again be incubated for 4 hours. After this step, 1 to 2 drops of the micro-organism suspension are removed and diluted with sterile physiological sodium chloride solution. The step of the 4 hour incubation in Mueller-Hinton broth could certainly take place in a device according to the present invention. The following procedure is, in principle, conceivable: bacteriological screening with CLED or MacConkey agar, i.e., from one side of the carrier body, the flexible film is completely removed, inoculating off and spreading out on to a further MacConkey agar, for example, in the case of gram-negative bacteria, so that 3 of the 4 troughs of the carrier body are now needed. The dilution spreading, which is normally otherwise carried out on plates, is carried out on the nutrient substrate substance in one of the 4 troughs. After obtaining the individual colonies, it is again possible to inoculate off and to incubate for 4 hours in the Mueller-Hinton broth, which is present in the fourth trough of the carrier body.

For use in industrial microbiology, it would be advisable as it were to overfill the troughs closed with flexible film so that, after pulling off the film, a use as dabbing-off dip is possible.

The carrier body can, as desired, be constructed as a plate with longitudinally arranged troughs on its surface or as a column with a segmented cross-section in the case of which the longitudinal segments form the troughs. The vessel can have an angular, circular or polygonal cross-section and the shapes of the carrier body and of the vessel can be combined with one another within the scope of the geometric possibilities.

In accordance with the invention, a device for the determination of micro-organisms comprises a vessel closable with a cover, and a cover for closing vessel. The device includes a nutrient medium carrier housed in the vessel and comprising a longitudinal carrier body which has a plurality of troughs for the reception of nutrient substrate substances. The device also includes removable cover means on said troughs and at least one closable filler connection, formed on the carrier body communicating with at least one trough.

For a better understanding of the present invention, together with other and further objects thereof, reference is made to the following description, taken in connection with the accompanying drawings, and its scope will be pointed out in the appended claims.

Referring now to the drawings:

FIG. 1 is a side view of a complete device for the determination of micro-organisms in a closed, storable state;

FIG. 2 is a longitudinal section through the hollow cylinder of the vessel;

FIG. 3 is a view of the broad side of the carrier body;

FIG. 4 is a view of the narrow side of the carrier body.

FIG. 5 is a top view of the carrier body according to FIGS. 3 and 4;

FIG. 6 is a lower view of the cap-shaped cover;

FIG. 7 is a longitudinal section through the cover according to FIG. 6;

FIG. 8 is a view from below of the plate carrying the plugs;

FIG. 9 is a side view of the plate according to FIG. 8;

FIG. 10 is a top view of the cover according to FIGS. 6 and 7 with the plate according to FIGS. 8 and 9;

FIG. 11 is a longitudinal section of the bottom of the vessel;

Figure 12:
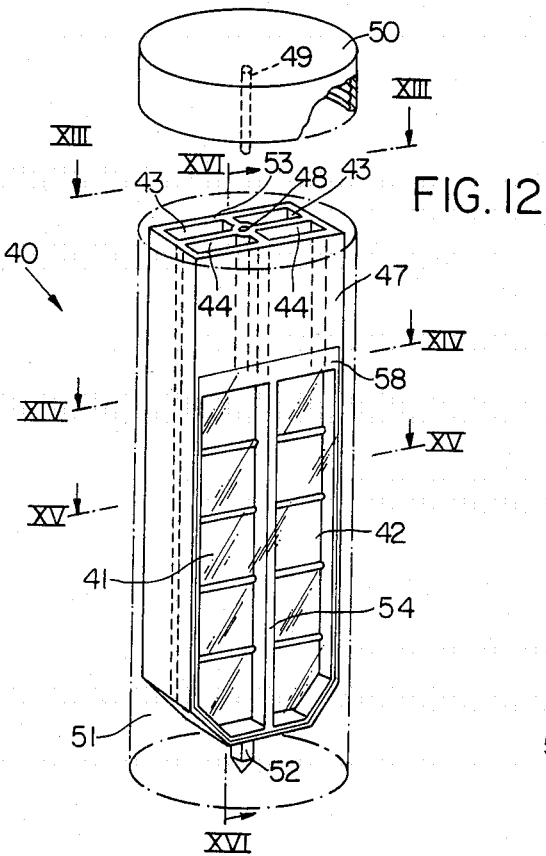
FIG. 12 is a perspective view of another embodiment of the present invention.

The device according to FIGS. 1 to 11 preferably comprises a vessel 1 in the form of a hollow cylinder of circular cross-section made of transparent synthetic resin material, and a plate-shaped carrier body 2, also made of synthetic resin material, which stands in the vessel 1, one end of which is closed by a cap-shaped cover 3 and the other end of which is closed by a stopper-like base 4.

The housing 1 preferably has, on its upper end above a shoulder 5, a triple outer thread 6. On its lower end, it preferably is provided internally with an annular recess 7 into which is fittingly inserted the stopper-like base 4, a lower annular flange 8 of which forms a stop for the end-face edge of the hollow cylinder of the housing 1. In the side of the base 4 facing the inner chamber of the housing 1 there preferably is provided a conical bottom trough 9 which runs at an acute angle of preferably 120° (FIG. 11).

The carrier body 2 preferably is made as a rectangular plate which, on one broad side, has two longitudinal troughs 10 and 11 running parallel to one another and, on the other broad side, preferably has two identical troughs 12 and 13. The four troughs 10, 11, 12 and 13 preferably have a common base plate 14 (FIG. 4) which is outwardly framed by an unbroken wall 15 which projects on both surfaces. A middle unbroken wall 16 on each surface of the base plate 14 preferably provides for the division into each of two troughs 10, 11 and 12, 13.

On the lower short end face 18a of the carrier body 2 there preferably is provided on the wall 16, a centering mandrel 17 which is pointed and which, when the device is assembled, engages in the apex of the conical trough 9 of the base 4. On the upper short end face 18 of the carrier body 2, the wall 15 outwardly preferably has a pyramidal shape and from each longer oblique face there preferably run off two filler connections 19 and 20, which run axially to the longitudinal axis of the carrier body 2. The filler connections 19 and 20 preferably are open at both ends. Each inner end preferably opens into one of the troughs 10, 11, 12 and 13 and, by staggered arrangement of the filler connections 19, 20 (FIG. 5), the filler connections 19 preferably are connected with the troughs 10 and 11 and the filler connections 20 with the troughs 12 and 13. The outer pyramidal surfaces of the wall 15 on the end face 18 preferably are each angled at 45°. On the side facing the troughs 10, 11, 12 and 13, the wall 15 preferably runs on both end surfaces 18, 18a at right-angles to the base plate 14. Alternatively, they can narrow down on the end face 18 towards the filler connections 19 or 20.

As closure of the housing 1, there preferably serves the cap-shaped cover 3 (FIGS. 6 to 10) which, in its circular-shaped circumferential wall 21, has a triple inner thread which cooperates with the outer thread 6 of the housing 1. From the inner surface of the bottom 3a of the cover 3 there preferably project collars 22, the arrangement of which corresponds to the arrangement of the filler connections 19 and 20 and which, for production-technical reasons, as well as for increasing the stability, preferably are connected with one another in one piece. When the cover is in the closed position, the collars 22 fit over the filler connections 19 and 20 and, together with the centering mandrel 17, hold the carrier body 2 firmly and centrally in the housing 1. Furthermore, in the bottom 3a of the cover 3 there preferably are formed passages 23 which align with the collars 22 so that these are open not only outwardly but also inwardly. Into the passages 23 and the collars 22 can be inserted plugs 24 which are carried by a plate 25 (FIGS. 8 and 9) and project at right-angles from this. Whereas the longitudinal sides of the plate 25 preferably run parallel, they preferably are rounded on their narrow sides and they preferably fit into a recess 26 in the outer surface of the bottom 3a of the cover 3 (FIGS. 7 and 10). When the plate 25 is introduced into the recess 26, the plugs 24 fittingly pass through the bottom 3a into the filler connections 19 and 20 and close them in the manner of stoppers.

For the preparation of the device for the qualitative and quantitative determination of micro-organisms, under sterile conditions, each trough 10, 11, 12 and 13 of the carrier body 2 preferably is closed with a film strip 30, which can be pulled off individually, and preferably is firmly welded on the edge of the wall 15. The carrier body 2 is then placed into the vessel 1, again under sterile conditions, and the collars 22 of the cover 3 are aligned to the filler connections 19, 20 and the cover 3 is screwed on to the housing 1. The plate 25 with the plugs 24 is removed from the cover 3 and through the open passages 23 and the filler connections 19 and 20 hollow needles are inserted, through which the troughs 10, 11, 12 and 13 are mechanically filled with any desired, possibly different nutrient substrate substances. As soon as the filling procedure is finished, the plate 25 is connected with the cover 3 and the plugs 24 close the filler connections 19 and 20. In this state, the device is stored and the parts thereof needed for the determination of micro-organisms are satisfactorily sterile until used. The nutrient substrate substances have the correct consistency and property and the surfaces thereof, when made ready for use by pulling off the films 30, are undamaged.

Figure 13:
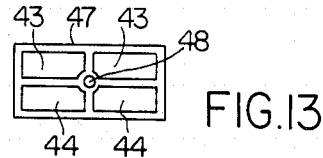
FIGS. 13, 14 and 15 are cross-sections along the lines XIII—XIII, XIV—XIV, and XV—XV, respectively, of FIG. 12.
Figure 14:
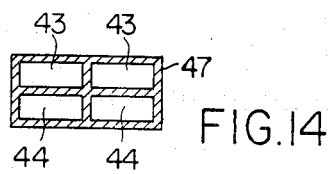
Figure 15:
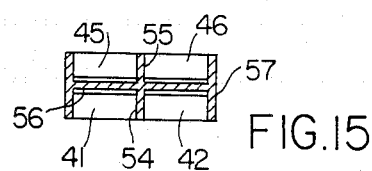
Figure 16:
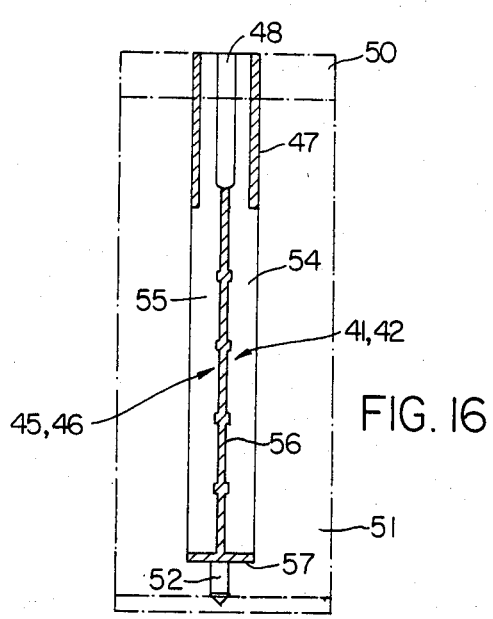
FIG. 16 is a cross-section along the line XVI—XVI of FIG. 12.

In the case of the embodiment of the present invention illustrated in FIGS. 12 to 16 of the accompanying drawings, the carrier body and filler connections have been modified.

The device thereby preferably comprises a vessel 51 in the form of a hollow cylinder of circular cross-section made of a transparent synthetic resin and of a plate-shaped carrier body 40, also made of a synthetic resin, which stands in the vessel 51. The carrier body 40 preferably is constructed as a rectangular plate with rectangular cross-section which, on one broad side, has two parallel, longitudinal troughs 41 and 42 and, on the other broad side, has two identical longitudinal troughs 45 and 46. The four troughs 41, 42, 45 and 46 preferably have a common base plate 56 (FIGS. 15 and 16) which is outwardly framed by an unbroken wall 57 which projects on both surfaces and extends up to the end of the carrier body 40. Middle walls 54 and 55 on each surface of the base plate 56 preferably provide for the subdivision into two troughs 41 and 42 on one surface of the base plate 56 and into two troughs 45 and 46 on the other surface of the base plate 56. The walls 54 and 55, together with the base plate 56, preferably are as wide as the wall 57. On the bottom end of the carrier body 40 there preferably is provided a centering mandrel 52 which serves the same purpose as the centering mandrel 17 in the embodiment illustrated in FIGS. 1 to 11.

On the upper end of the carrier body 40 there preferably are provided filler connections 43 and 44, each of which has a rectangular cross-section. They comprise a continuation of the troughs 41, 42, 45 and 46 which, to a certain extent, is surrounded by an encompassing wall 47 which terminates flatly at the openings of the filler connections 43 and 44. Corresponding to the arrangement of the troughs 41, 42, 45 and 46, the filler connections 43 and 44 preferably are also arranged in pairs on each surface of the base plate 56. At the intersection of the four troughs there preferably is provided in the base plate 56 an axial blind hole 48, the length of which corresponds approximately to the axial extension of the encompassing wall 47. This blind hole 48 serves for the reception of a pointed pin 49 which projects from the center of a screw cover 50 for the vessel 51.

The pairs of troughs 41, 42 and 45, 46 preferably are each covered with a flexible film 58 which is welded to the surrounding wall 57 and to the middle walls 54 and 55. Nutrient substrate substance is then injected through the filler connections 43 and 44 into the four troughs 41, 42, 45 and 46 and the rectangular openings of the filler connections 43 and 44, as well as the blind hole 48, preferably are covered with a flexible film 53 which preferably is firmly welded on to the edge of the surrounding wall 57 and on to walls 54, 55 and 56, for example by ultra-sonics. Screw cap 50 is then placed on to the carrier body 40 in such a manner that the pin 49 passes into the blind hole 48, the film 53 being penetrated at this point. Subsequently, the carrier body 40 is placed into the vessel 51 and cover 50 is screwed on to the opening of the vessel 51. All the steps can be carried out under sterile conditions.

While there have been described what are at present considered to be the preferred embodiments of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. A device for the determination of micro-organisms, comprising:
   a vessel closable with a cover;
   a cover for closing said vessel;
   a nutrient medium carrier housed in said vessel and comprising a longitudinal carrier body which has a plurality of troughs for the reception of nutrient substrate substances;
   removable cover means on said troughs;
   one or more closable filler connections, formed on said carrier body, communicating with at least one trough, and
   all said troughs continuing up to said filler connections of said carrier body, said filler connections being partially formed by a common encompassing wall which follows the cross-sectional shape of said carrier body.

2. A device for the determination of micro-organisms, comprising:
   a vessel closable with a cover;
   a cover for closing said vessel;
   a nutrient medium carrier housed in said vessel and comprising a longitudinal carrier body which has a plurality of troughs for the reception of nutrient substrate substances;
   removable cover means on said troughs;
   one or more closable filler connections, formed on said carrier body, communicating with at least one trough;
   all said troughs continuing up to said filler connections of said carrier body, said filler connections being partially formed by a common encompassing wall which follows the cross-sectional shape of said carrier body; and
   said filler connections intersecting and, at the intersection thereof, including a blind hole, and said cover being screwable and including an axial pin which projects therefrom for engagement with said blind hole.

* * * * *